US012751390B2

(12) United States Patent
Haarsma et al.

(10) Patent No.: US 12,751,390 B2
(45) Date of Patent: Oct. 6, 2026

(54) FUSARIUM RESISTANCE IN CELERY

(71) Applicant: Bejo Zaden B.V., Warmenhuizen (NL)

(72) Inventors: Adriana Dorien Haarsma, Warmenhuizen (NL); Jacob van Dorp, Warmenhuizen (NL); Jordi Cornelis Boshoven, Warmenhuizen (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 377 days.

(21) Appl. No.: 18/269,321

(22) PCT Filed: Dec. 23, 2021

(86) PCT No.: PCT/EP2021/087513
§ 371 (c)(1),
(2) Date: Jun. 23, 2023

(87) PCT Pub. No.: WO2022/136652
PCT Pub. Date: Jun. 30, 2022

(65) Prior Publication Data
US 2024/0224911 A1 Jul. 11, 2024

(51) Int. Cl.
*A01H 5/10* (2018.01)
*A01H 1/00* (2006.01)
*A01H 1/04* (2006.01)
*A01H 6/06* (2018.01)

(52) U.S. Cl.
CPC ............. *A01H 6/064* (2018.05); *A01H 1/045* (2021.01); *A01H 1/1255* (2021.01); *A01H 5/10* (2013.01)

(58) Field of Classification Search
None
See application file for complete search history.

(56) References Cited

U.S. PATENT DOCUMENTS

2010/0235941 A1 9/2010 Foncelle et al.
2023/0337612 A1 10/2023 Pierce

FOREIGN PATENT DOCUMENTS

CN 103789417 A 5/2014
CN 109152345 A 1/2019
CN 116828978 A 9/2023

OTHER PUBLICATIONS

Epstein, 2017, "Breeding of Disease-Resistant Celery".*
Bruznican et al., "Celery and Celeriac: A Critical View on Present and Future Breeding", Frontiers in Plant Science, 2020, Article 1899, vol. 10, Frontiers in Plant Science.
Epstein, "Breeding of Disease-Resistant Celery", 2017.
Epstein et al., "Fusarium wilt in celery and cilantro in Ventura county", California Celery Research Advisory Board, 2020.
Huestis et al., "Development of Genetic Markers in Celery Based on Restriction Fragment Length Polymorphisms", Theoretical and Applied Genetics, 1993, pp. 889-896, vol. 85, Springer-Verlag.

* cited by examiner

*Primary Examiner* — Jason Deveau Rosen
(74) *Attorney, Agent, or Firm* — The Webb Law Firm

(57) ABSTRACT

Provided herein are *Apium graveolens* plants resistant to the plant pathogen *Fusarium oxysporum* f. sp. *Apii* race 4 and wherein the resistance is encoded by one genomic region or a combination of at least two, or three genomic regions. Also provided herein are methods for identifying the present *Fusarium oxysporum* f. sp. *Apii* race 4 resistant plants and to molecular markers for use in the present methods.

9 Claims, No Drawings

Specification includes a Sequence Listing.

SEQUENCE LISTING

<160> NUMBER OF SEQ ID NOS: 36

<210> SEQ ID NO 1
<211> LENGTH: 101
<212> TYPE: DNA
<213> ORGANISM: Apium graveolens

<400> SEQUENCE: 1
gctgttgggt gggagagagt atggaagagt ttacaaagga tgggttcagg ggaagacgta 60
caccccgtct aggcacgatg ttggaacaac cattgcagtt a 101

<210> SEQ ID NO 2
<211> LENGTH: 101
<212> TYPE: DNA
<213> ORGANISM: Apium graveolens

<400> SEQUENCE: 2
gctgttgggt gggagagagt atggaagagt ttacaaagga tgggttcagg agaagacgta 60
caccccgtct aggcacgatg ttggaacaac cattgcagtt a 101

<210> SEQ ID NO 3
<211> LENGTH: 101
<212> TYPE: DNA
<213> ORGANISM: Apium graveolens

<400> SEQUENCE: 3
aacaggaacc acacgtggtt tcccttcatg agaaacagga ccattaggtg ccttctgttt 60
atgacatgaa gcaggaatat tagttggctt aggtttctta g 101

<210> SEQ ID NO 4
<211> LENGTH: 101
<212> TYPE: DNA
<213> ORGANISM: Apium graveolens

<400> SEQUENCE: 4
aacaggaacc acacgtggtt tcccttcatg agaaacagga ccattaggtg tcttctgttt 60
atgacatgaa gcaggaatat tagttggctt aggtttctta g 101

<210> SEQ ID NO 5
<211> LENGTH: 101
<212> TYPE: DNA
<213> ORGANISM: Apium graveolens

<400> SEQUENCE: 5
tgtttagagg caagaaatca agaaaagatg aaatcttggg gatttttagt ctgtgtttgt 60
stgtgtgtga attgggttgg agtgaattct tggtaaaaag a 101

<210> SEQ ID NO 6
<211> LENGTH: 101
<212> TYPE: DNA
<213> ORGANISM: Apium graveolens

<400> SEQUENCE: 6
tgtttagagg caagaaatca agaaaagatg aaatcttggg gatttttagt gtgtgtttgt 60
stgtgtgtga attgggttgg agtgaattct tggtaaaaag a 101

<210> SEQ ID NO 7
<211> LENGTH: 101
<212> TYPE: DNA
<213> ORGANISM: Apium graveolens

<400> SEQUENCE: 7
acgacaaatt actacagttt gcttcaatct tgccaaatcg tgtgaagcta acacatgttg 60
aaataccatg tccttttcta tttttaaagt tatcgtttta g 101

<210> SEQ ID NO 8
<211> LENGTH: 101
<212> TYPE: DNA
<213> ORGANISM: Apium graveolens

<400> SEQUENCE: 8
acgacaaatt actacagttt gcttcaatct tgccaaatcg tgtgaagcta gcacatgttg 60
aaataccatg tccttttcta tttttaaagt tatcgtttta g 101

<210> SEQ ID NO 9
<211> LENGTH: 101
<212> TYPE: DNA
<213> ORGANISM: Apium graveolens

<400> SEQUENCE: 9
gtgttagagt taacaaagtt ggcagaaacc aagtgcactg atccaacgtt gtgggctaya 60
gaagtgtcaa ctactttaaa ctcagctgca gtggacttgc c 101

<210> SEQ ID NO 10
<211> LENGTH: 101
<212> TYPE: DNA
<213> ORGANISM: Apium graveolens

<400> SEQUENCE: 10
gtgttagagt taacaaagtt ggcagaaacc aagtgcactg atccaacgtt atgggctaya 60
gaagtgtcaa ctactttaaa ctcagctgca gtggacttgc c 101

<210> SEQ ID NO 11
<211> LENGTH: 101
<212> TYPE: DNA
<213> ORGANISM: Apium graveolens

<400> SEQUENCE: 11
cacaaacccc ccttcatttc atttctcatt tctcatttct catttctcac aattcactca 60
actctctcgt aatctccgat cccaatttca cccccacaat g 101

<210> SEQ ID NO 12
<211> LENGTH: 101
<212> TYPE: DNA
<213> ORGANISM: Apium graveolens

<400> SEQUENCE: 12
cacaaacccc ccttcatttc atttctcatt tctcatttct catttctcac gattcactca 60
actctctcgt aatctccgat cccaatttca cccccacaat g 101

<210> SEQ ID NO 13
<211> LENGTH: 101
<212> TYPE: DNA
<213> ORGANISM: Apium graveolens

<400> SEQUENCE: 13
aagtacctgt tctagtgagt ttatctacct cctgtcaatc tttttccttt tttgttttct 60
ggtacttgga ccaaaacccc aagtgtataa acgtcaggtc t 101

<210> SEQ ID NO 14
<211> LENGTH: 101
<212> TYPE: DNA
<213> ORGANISM: Apium graveolens

<400> SEQUENCE: 14
aagtacctgt tctagtgagt ttatctacct cctgtcaatc tttttccttt cttgttttct 60
ggtacttgga ccaaaacccc aagtgtataa acgtcaggtc t 101

<210> SEQ ID NO 15
<211> LENGTH: 101
<212> TYPE: DNA
<213> ORGANISM: Apium graveolens

<400> SEQUENCE: 15
gggacatagc attcaggatt tataagagtc tggaaagtgc tattttcacc ccccacaaga 60
tcctgaagtg caatctcaat aattctttca ttctccctgc t 101

<210> SEQ ID NO 16
<211> LENGTH: 101
<212> TYPE: DNA
<213> ORGANISM: Apium graveolens

<400> SEQUENCE: 16
gggacatagc attcaggatt tataagagtc tggaaagtgc tattttcacc acccacaaga 60
tcctgaagtg caatctcaat aattctttca ttctccctgc t 101

<210> SEQ ID NO 17
<211> LENGTH: 101
<212> TYPE: DNA
<213> ORGANISM: Apium graveolens

<400> SEQUENCE: 17
atagagaagg atataacaaa atattggaaa atgccaagcc ccgaaatgat ccatatggga 60
ggcatttatc tgcctttacc tacctccggc tcagctcctt g 101

<210> SEQ ID NO 18
<211> LENGTH: 101
<212> TYPE: DNA
<213> ORGANISM: Apium graveolens

<400> SEQUENCE: 18
atagagaagg atataacaaa atattggaaa atgccaagcc ccgaaatgat tcatatggga 60
ggcatttatc tgcctttacc tacctccggc tcagctcctt g 101

<210> SEQ ID NO 19
<211> LENGTH: 101
<212> TYPE: DNA
<213> ORGANISM: Apium graveolens

<400> SEQUENCE: 19
taccatatga ctgtgccgag ggaggaaatg caagcagaag tcctagtttt taaattccaa 60
ggtgtggcag tagtcccagt gagtgtcgta ttgtagattt t 101

<210> SEQ ID NO 20
<211> LENGTH: 101
<212> TYPE: DNA
<213> ORGANISM: Apium graveolens

<400> SEQUENCE: 20
taccatatga ctgtgccgag ggaggaaatg caagcagaag tcctagtttt aaaattccaa 60
ggtgtggcag tagtcccagt gagtgtcgta ttgtagattt t 101

<210> SEQ ID NO 21
<211> LENGTH: 101
<212> TYPE: DNA
<213> ORGANISM: Apium graveolens

<400> SEQUENCE: 21
atctccagag tcgttgccac agctggcaga gattgctagg aatcctgctg ctttatctga 60
acttactgtt gggaaagagg ataacttgag acattctaga g 101

<210> SEQ ID NO 22
<211> LENGTH: 101
<212> TYPE: DNA
<213> ORGANISM: Apium graveolens

<400> SEQUENCE: 22
atctccagag tcgttgccac agctggcaga gattgctagg aatcctgctg ttttatctga 60
acttactgtt gggaaagagg ataacttgag acattctaga g 101

<210> SEQ ID NO 23
<211> LENGTH: 101
<212> TYPE: DNA
<213> ORGANISM: Apium graveolens

<400> SEQUENCE: 23
cagaaatatg atgcttagat atggtcttac tgttaccata ctattaaccc gttaaaagca 60
aatatgttag gagaccaatt acaacaaaaa gatcaccacc a 101

<210> SEQ ID NO 24
<211> LENGTH: 101
<212> TYPE: DNA
<213> ORGANISM: Apium graveolens

<400> SEQUENCE: 24
cagaaatatg atgcttagat atggtcttac tgttaccata ctattaaccc attaaaagca 60
aatatgttag gagaccaatt acaacaaaaa gatcaccacc a 101

<210> SEQ ID NO 25
<211> LENGTH: 101
<212> TYPE: DNA
<213> ORGANISM: Apium graveolens

<400> SEQUENCE: 25
ttaaagcctc ttatgcaacc aagtaacaaa aatcaaaagt gaggattcga cctaattgga 60
tttgaatttg ggagttttga aatctaaggt tgaatttggg g 101

<210> SEQ ID NO 26
<211> LENGTH: 101
<212> TYPE: DNA
<213> ORGANISM: Apium graveolens

<400> SEQUENCE: 26
ttaaagcctc ttatgcaacc aagtaacaaa aatcaaaagt gaggattcga tctaattgga 60
tttgaatttg ggagttttga aatctaaggt tgaatttggg g 101

<210> SEQ ID NO 27

<211> LENGTH: 101
<212> TYPE: DNA
<213> ORGANISM: Apium graveolens

<400> SEQUENCE: 27
atatcccctt gggtggagct actcttagtt gcgcagcact tatttagctt gttttggaag 60
gtgtccaaaa acaaattcat taggtctgct tagcaaagcc c 101

<210> SEQ ID NO 28
<211> LENGTH: 101
<212> TYPE: DNA
<213> ORGANISM: Apium graveolens

<400> SEQUENCE: 28
atatcccctt gggtggagct actcttagtt gcgcagcact tatttagctt attttggaag 60
gtgtccaaaa acaaattcat taggtctgct tagcaaagcc c 101

<210> SEQ ID NO 29
<211> LENGTH: 101
<212> TYPE: DNA
<213> ORGANISM: Apium graveolens

<400> SEQUENCE: 29
ttttgtgcgg attgtagtaa aaaacttggc tgtcaagtat tcgagtactt craaaaattc 60
agacacttca ttttactgca agatgaagat caagaatctc g 101

<210> SEQ ID NO 30
<211> LENGTH: 101
<212> TYPE: DNA
<213> ORGANISM: Apium graveolens

<400> SEQUENCE: 30
ttttgtgcgg attgtagtaa aaaacttggc tgtcaagtat tcgagtactt traaaaattc 60
agacacttca ttttactgca agatgaagat caagaatctc g 101

<210> SEQ ID NO 31
<211> LENGTH: 87
<212> TYPE: DNA
<213> ORGANISM: Apium graveolens

<400> SEQUENCE: 31
taatgagcgt gaggtggaag cagctgggaa tggaaattta acctccaatg tagaaaagag 60
ttctaatggt caattagaaa caaaaaa 87

<210> SEQ ID NO 32
<211> LENGTH: 87
<212> TYPE: DNA
<213> ORGANISM: Apium graveolens

<400> SEQUENCE: 32
taatgagcgt gaggtggaag cagctgggaa tggaaattta acctccaatg cagaaaagag 60
ttctaatggt caattagaaa caaaaaa 87

<210> SEQ ID NO 33
<211> LENGTH: 101
<212> TYPE: DNA
<213> ORGANISM: Apium graveolens

<400> SEQUENCE: 33
gcaaaagtag gctcctgaca ttgtacttat ataaattgca ctttactgaa ggcgtaattc 60

```
ttctactact aatctggaat ccagtctaaa gagccactgt g                    101


<210> SEQ ID NO 34
<211> LENGTH: 101
<212> TYPE: DNA
<213> ORGANISM: Apium graveolens

<400> SEQUENCE: 34

gcaaaagtag gctcctgaca ttgtacttat ataaattgca ctttactgaa agcgtaattc     60

ttctactact aatctggaat ccagtctaaa gagccactgt g                    101


<210> SEQ ID NO 35
<211> LENGTH: 101
<212> TYPE: DNA
<213> ORGANISM: Apium graveolens

<400> SEQUENCE: 35

aaggaagaaa tcaccagtgg cytcagcaaa tgactttttg ggaggtgggg caggagagag     60

atttggggga ggtgaagatg aggctttgat gaggtggagg t                    101


<210> SEQ ID NO 36
<211> LENGTH: 101
<212> TYPE: DNA
<213> ORGANISM: Apium graveolens

<400> SEQUENCE: 36

aaggaagaaa tcaccagtgg cytcagcaaa tgactttttg ggaggtgggg taggagagag     60

atttggggga ggtgaagatg aggctttgat gaggtggagg t                    101
```

FUSARIUM RESISTANCE IN CELERY

CROSS-REFERENCE TO RELATED APPLICATIONS

This application is the United States national phase of International Application No. PCT/EP2021/087513 filed Dec. 23, 2021, and claims priority to International Application No. PCT/EP2020/087870 filed Dec. 24, 2020, the disclosures of which are hereby incorporated by reference in their entireties.

The Sequence Listing associated with this application is filed in electronic format via EFS-Web and is hereby incorporated by reference into the specification in its entirety. The name of the text file containing the Sequence Listing is 2304398_ST25.txt. The size of the text file is 8,574 bytes, and the text file was created on May 11, 2023.

BACKGROUND OF THE INVENTION

Field of the Invention

The present invention relates to *Apium graveolens* plants, wherein the plants are resistant to the plant pathogen *Fusarium oxysporum* f. sp. *Apii* race 4 and wherein the resistance is encoded by one genomic region, or a combination of at least two, or three genomic regions. The present invention further relates methods for identifying the present *Fusarium oxysporum* f. sp. *Apii* race 4 resistant plants and to molecular markers for use in the present methods.

Description of Related Art

Celery (*Apium graveolens*) is a member of the Apiaceae family, a family of aromatic flowering plants that includes carrot, parsnip, parsley, coriander, fennel and dill. Three types of celery, which are morphologically distinct, are generally cultivated. Celery or stalk celery (*A. graveolens* var. *dulce*) is grown for its long solid petioles (leaf stalks), celeriac (*A. graveolens* var. *rapaceum*) for its thickened stem (hypocotyl), and leaf celery (*A. graveolens* var. *secalinum*), which has thin stalks, for its leaves.

Celery is a popular vegetable and eaten around the world. Celery is used, for example, in salads, soups and stews. In North America and Europe, the crisp petiole (leaf stalk) of celery is usually eaten raw or used as an ingredient in salads, juices and soups. In Europe, the thickened hypocotyl of celeriac is shredded and used in salads. Celery leaves have a strong flavor and are mostly used to season soups or stews, or as a dried herb. Celery seeds contain various substances with potentially health-promoting properties. They are, therefore, used as a substance in dietary supplements and alternative medicine. Celery seeds can also be crushed and mixed with salt to produce celery salt for the seasoning of food. In some cases, celery salt is also made from an extract of the roots or using dried leaves.

Celery has a long history of cultivation. Celery was first used as a food during the 16th century in Italy, and Linnaeus described the plant in his Species *Plantarum* in 1753.

Celery is presumably native to the salt marshes in Europe and the Mediterranean but currently grows in many regions around the world, including the Mediterranean, Australia, South Africa and South America. The largest producer of stalk celery is the USA, especially the state of California, followed by Mexico. Celeriac is predominantly grown in Europe, and Chinese or leaf celery is the most common type of celery grown in Asia. Celery grows best in temperate climates with mild or cool weather.

Wild celery, known as smallage, can grow up to 1 meter. It has a furrowed stalk with wedge-shaped leaves. The whole plant has a strong, earthy taste and a distinctive smell.

Celery plants are grown from seed and sown in a hot bed or the open garden depending on the season. When the plants reach a height of 15 to 20 cm, they are planted out in deep trenches, which are gradually filled up with soil to limit exposure to the sun. This process is called blanching, and yields plants that are less bitter and have a mild, sweet and aromatic taste. Several modern cultivars will blanch spontaneously without this treatment and are called self-blanching.

Due to the very high uniformity of modern cultivars, fields are only harvested once, roughly three months after planting. After removal of the leaves and stalks, celery can be stored for several weeks at temperatures between 0 to 2° C.

Like most crops, various pathogens challenge the cultivation of celery and celeriac. Examples are the ascomycete fungus *Septoria apiicola* which causes celery leaf spot or late blight, and the fungus *Cercospora apii*, the cause of early blight. Other pathogens are viruses, such as Celery Mosaic Virus (CeMV), and several insects, like leaf miners and shield bugs (*Graphosoma* sp.). However, worldwide, *Fusarium* yellows, also known as *Fusarium* blight or *Fusarium* wilt, caused by the ascomycete fungus *Fusarium oxysporum* is considered the economically most important disease.

The fungus *F. oxysporum* is commonly found in soil and contains both pathogenic and non-pathogenic strains. Although *F. oxysporum* has a broad host range, strains display pathogenicity on a limited range of hosts. This observation has led to the concept of formae speciales (*forma specialis*, f. sp.), which distinguishes particular forms of the species based on their adaptation to different hosts. For example, strains responsible for *Fusarium* yellows in celery belong to the *forma specialis apii*. The *forma specialis apii* contains four races that are distinguished from each other by differences in the pathogenicity at the cultivar-level.

Historically, *F. oxysporum* has caused substantial losses to celery growers until the resistant celery cultivar, Tall Utah 52-70, was introduced in the late 1950s. At that time, only a single race of *F. oxysporum* f. sp. *apii* (Foa1) existed to which green cultivars of celery, especially Tall Utah 52-70, had excellent resistance. As a result, the disease was no longer a problem. However, in 1976, a new *F. oxysporum* f. sp. *apii* race, termed race 2 (Foa2), was isolated to which the green cultivars were not resistant. Breeders identified a genetic resistance to Foa2 in the celeriac accession PI 169001 and Foa2-tolerant celery cultivars, like Challenger, were generated. Recently, however, yet another new highly virulent race of *F. oxysporum* f. sp. *apii* appeared in California, USA, called race 4 (Foa4), to which Foa2-resistant cultivars, like Challenger, were also not resistant. Although initially identified in a single field in California, USA, this new race of *F. oxysporum* continues to spread.

The fungus *F. oxysporum* infects the plants through the root system. Accumulation of fungal biomass in the vascular system of the plant results in reduced water uptake and discoloration of the inner roots. Symptoms of a mild or late infection are slight stunting and stiffening of the outer stalks. In severe cases, the outer leaves turn yellow, followed by the rest of the foliage. There is progressive wilting, which eventually leads to the complete loss of the plant. The severity of *Fusarium* yellows is linked to disease pressure and worsened by warm weather and heavy, wet soils.

The fungus *F. oxysporum* can spread to disease-free fields by the movement of contaminated soil, e.g. via farm equipment or by wind or water. The fungus can also be present on seeds and seedling transplants.

Soil-applied fungicides can prevent or reduce the effects of infection by *F. oxysporum*. However, these fungicides usually have limited efficacy. Moreover, an increasing number of countries in Europe have a policy aimed at reducing the use of crop protection agents, and there is a growing demand for organically grown crops due to public concerns about the effect of pesticides on human health and the environment.

Alternative approaches, such as short-term fallowing of infested fields and crop rotation schemes using lettuce or onion, are not effective control measures. The fungus *F. oxysporum* can survive for long periods in the soil as dormant spores or even multiply in the roots of non-susceptible host plants, including many weeds.

Improvements in the yield and quality of the crop, as well as a reduction in the application of fungicides, can be achieved by developing *A. graveolens* plants with better tolerance or resistance to *F. oxysporum*. There is, therefore, a need in the field to provide *A. graveolens* plants with an improved and broader tolerance or resistance to *F. oxysporum*, the causal agent of *Fusarium* yellows.

In general, breeding for resistance starts by making a cross between a source of resistance and susceptible genetic material with a high level of agronomical quality. Resistant offspring is selected using DNA markers and repeatedly backcrossed to the agronomically elite parent line. This process ultimately leads to resistant plants with desirable agronomic characteristics.

SUMMARY OF THE INVENTION

Considering the above, it is an object of the present invention, amongst other objects to obviate the above problems in the prior art and especially to provide *Apium graveolens* plants being resistant to the plant pathogen *Fusarium oxysporum* f. sp. *Apii* race 4.

The present invention meets the above object, amongst other objects, through the plants as outlined in the appended claims.

Specifically, this object, amongst other objects, is achieved by providing *Apium graveolens* plants wherein the plants are resistant to the plant pathogen *Fusarium oxysporum* f. sp. *Apii* race 4, and wherein the resistance is encoded by a combination of at least two genomic regions, one genomic region is located on linkage group 4 between 28 and 33 cM; and one genomic region is located on linkage group 5 between 56 and 60 cM.

Specifically, this object, amongst other objects, is alternatively achieved by providing *Apium graveolens* plants wherein the plants are resistant to the plant pathogen *Fusarium oxysporum* f. sp. *Apii* race 4, and wherein the resistance is encoded by a at least one genomic region located on linkage group 4 between 28 and 33 cM.

Specifically, this object, amongst other objects, is alternatively achieved by providing *Apium graveolens* plants wherein the plants are resistant to the plant pathogen *Fusarium oxysporum* f. sp. *Apii* race 4, and wherein the resistance is encoded by at least one genomic region located on linkage group 5 between 56 and 60 cM.

Specifically, this object, amongst other objects, is alternatively achieved by providing *Apium graveolens* plants wherein the plants are resistant to the plant pathogen *Fusarium oxysporum* f. sp. *Apii* race 4, and wherein the resistance is encoded by at least one genomic region located on linkage group 7 between 24 and 38 cM.

Specifically, this object, amongst other objects, is alternatively achieved by providing *Apium graveolens* plants wherein the plants are resistant to the plant pathogen *Fusarium oxysporum* f. sp. *Apii* race 4, and wherein the resistance is encoded by a combination of at least two genomic regions, one genomic region is located on linkage group 5 between 56 and 60 cM and one genomic region located on linkage group 7 between 24 and 38 cM.

Specifically, this object, amongst other objects, is alternatively achieved by providing *Apium graveolens* plants wherein the plants are resistant to the plant pathogen *Fusarium oxysporum* f. sp. *Apii* race 4, and wherein the resistance is encoded by a combination of at least two genomic regions, one genomic region is located on linkage group 4 between 28 and 33 cM and one genomic region located on linkage group 7 between 24 and 38 cM.

Specifically, this object, amongst other objects, is achieved by providing *Apium graveolens* plants wherein the plants are resistant to the plant pathogen *Fusarium oxysporum* f. sp. *Apii* race 4, and wherein the resistance is encoded by a combination of at least three genomic regions, one genomic region is located on linkage group 4 between 28 and 33 cM, one genomic region is located on linkage group 5 between 56 and 60 cM, and one genomic region located on linkage group 7 between 24 and 38 cM.

DESCRIPTION OF THE INVENTION

Although the present genomic fragments can be introduced into *A. graveolens* plants by introgression, these genomic fragments can also be artificially introduced in plant cells to generate Foa4-resistant *A. graveolens* plants using various genome engineering techniques.

As the genomic regions are known, these genomic fragments can, for example, be transferred between plants using microplast-mediated chromosome transfer. Using this method, entire chromosomes or parts thereof can be horizontally transferred between plants. First, micro-protoplasts containing one or a few chromosomes that carry the resistance are generated. Subsequently, the micro-protoplasts are fused with protoplasts generated from a susceptible *A. graveolens* plant. This method produces plants with monosomic additions, which can subsequently be crossed with other plants to generate Foa4-resistant lines.

Alternatively, as the nucleotide sequences of the present genomic fragments are known, these fragments can also be artificially assembled in yeast and subsequently allowed to recombine with the *A. graveolens* genome. The genomic fragments can also be amplified by long-range PCR amplifications or de novo synthesized and the resulting fragments can be cloned and transformed into *A. graveolens* cells in a single step or in a series of transformations ultimately resulting in the present *A. graveolens* plants. The present genomic fragments, completely or in parts later to be reassembled, can also be isolated from gels or columns, for example, after restriction digestion, and subsequently transformed into *A. graveolens* cells.

Yet alternatively, the genomic fragments of interest can be introduced into a vector under a (strong) promotor. Subsequently, susceptible plants can be transformed with the vector and the sequence of interest would be expressed resulting in resistance. These techniques are readily available for the skilled person. Construction of artificial chromosomes comprising the present genomic fragments is also contemplated within the context of the present invention.

According to a preferred embodiment of the present invention, the present genomic region or regions is/are obtainable, obtained, or is/are from an *Apium graveolens* plant deposited under deposit number NCIMB 43699. An *Apium graveolens* plant comprising one genomic region located on linkage group 4 between 28 and 33 cM, one genomic region located on linkage group 5 between 56 and 60 cM, and one genomic region located on linkage group 7 between 24 and 38 cM was deposited at NCIMB (National Collections of Industrial, Food and Marine Bacteria; NCIMB Limited, Ferguson Building; Craibstone Estate, Bucksburn Aberdeen, Scotland, AB21 9YA United Kingdom) on 30 Nov. 2020 under deposit number NCIMB 43699.

The present *Apium graveolens* plants preferably comprise in their genome at least one sequence selected from the group consisting of SEQ ID No. 1, SEQ ID No. 3, SEQ ID No. 5, SEQ ID No. 7, and SEQ ID No. 9. The present sequences represent the resistance providing allele while plants comprising in their genome at least one sequence selected from the group consisting of SEQ ID No. 2, SEQ ID No. 4, SEQ ID No. 6, SEQ ID No. 8, and SEQ ID No. 10 comprise the susceptible allele.

The present *Apium graveolens* plants preferably further comprise in their genome at least one sequence selected from the group consisting of SEQ ID No. 11, SEQ ID No. 13, SEQ ID No. 15, SEQ ID No. 17, SEQ ID No. 19, SEQ ID No. 21, SEQ ID No. 23, SEQ ID No. 25, and SEQ ID No. 27.

The present sequences represent the resistance providing allele while plants comprising in their genome at least one sequence selected from the group consisting of SEQ ID No. 12, SEQ ID No. 14, SEQ ID No. 16, SEQ ID No. 18, SEQ ID No. 20, SEQ ID No. 22, SEQ ID No. 24, SEQ ID No. 26, and SEQ ID No. 28 comprise the susceptible allele.

The present *Apium graveolens* plants further preferably comprise in their genome at least one sequence selected from the group consisting of SEQ ID No. 29, SEQ ID No. 31, SEQ ID No. 33, and SEQ ID No. 35. The present sequences represent the resistance providing alleles while plants comprising in their genome at least one sequence selected from the group consisting of SEQ ID No. 30, SEQ ID No. 32, SEQ ID No. 34, and SEQ ID No. 36 comprise the susceptible allele.

The present *Apium graveolens* plants more preferably comprise in their genome at least one sequence selected from the group consisting of SEQ ID No. 1, SEQ ID No. 3, SEQ ID No. 5, SEQ ID No. 7, SEQ ID No. 9, i.e. linkage group 4, and at least one sequence selected from the group consisting of SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, i.e. linkage group 5 and/or at least one sequence selected from the group consisting of SEQ ID No. 29, SEQ ID No. 31, SEQ ID No. 33, SEQ ID No. 35, i.e. linkage group 7. The present sequences present the resistance providing alleles while plants comprising in their genome at least one sequence selected from the group consisting of SEQ ID No. 2, SEQ ID No. 4, SEQ ID No. 6, SEQ ID No. 8, and SEQ ID No. 10 and at least one sequence selected from the group consisting of SEQ ID No. 12, SEQ ID No. 14, SEQ ID No. 16, SEQ ID No. 18, SEQ ID No. 20, SEQ ID No. 22, SEQ ID No. 24, SEQ ID No. 26, and SEQ ID No. 28 and/or at least one sequence selected from the group consisting of SEQ ID No. 30, SEQ ID No. 32, SEQ ID No. 34, and SEQ ID No. 36 comprise susceptible alleles.

The present *Apium graveolens* plants most preferably comprise in their genome at least one sequence selected from the group consisting of SEQ ID No. 1, SEQ ID No. 3, SEQ ID No. 5, SEQ ID No. 7, SEQ ID No. 9, i.e. linkage group 4, and at least one sequence selected from the group consisting of SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, i.e. linkage group 5 and at least one sequence selected from the group consisting of SEQ ID No. 29, SEQ ID No. 31, SEQ ID No. 33, SEQ ID No. 35, i.e. linkage group 7. The present sequences present the resistance providing alleles while plants comprising in their genome at least one sequence selected from the group consisting of SEQ ID No. 2, SEQ ID No. 4, SEQ ID No. 6, SEQ ID No. 8, and SEQ ID No. 10 and at least one sequence selected from the group consisting of SEQ ID No. 12, SEQ ID No. 14, SEQ ID No. 16, SEQ ID No. 18, SEQ ID No. 20, SEQ ID No. 22, SEQ ID No. 24, SEQ ID No. 26, and SEQ ID No. 28 and at least one sequence selected from the group consisting of SEQ ID No. 30, SEQ ID No. 32, SEQ ID No. 34, and SEQ ID No. 36 comprise susceptible alleles.

The present *Apium graveolens* plants preferably comprise in their genome at least one sequence selected from the group consisting of SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, i.e. linkage group 5 and at least one sequence selected from the group consisting of SEQ ID No. 29, SEQ ID No. 31, SEQ ID No. 33, SEQ ID No. 35, i.e. linkage group 7. The present sequences present the resistance providing alleles while plants comprising in their genome at least one sequence selected from the group consisting of SEQ ID No. 12, SEQ ID No. 14, SEQ ID No. 16, SEQ ID No. 18, SEQ ID No. 20, SEQ ID No. 22, SEQ ID No. 24, SEQ ID No. 26, and SEQ ID No. 28 and at least one sequence selected from the group consisting of SEQ ID No. 30, SEQ ID No. 32, SEQ ID No. 34, and SEQ ID No. 36 comprise susceptible alleles.

According to a preferred embodiment, the present *Apium graveolens* plants are cytoplasmic male sterile (CMS).

According to yet another preferred embodiment, the present *Apium graveolens* plants are hybrid plants.

Preferably, the present *Apium graveolens* plants are selected from the group consisting of *Apium graveolens* var. *secalinum, Apium graveolens* var. *dulce*, and *Apium graveolens* var. *rapaceum.*

The present invention also relates to hybrid celery or celeriac obtainable by crossing *Fusarium oxysporum* f. sp. *apii* susceptible celery or celeriac with the present *Apium graveolens* plants or hybrid celery or celeriac obtainable by crossing a *Fusarium oxysporum* f. sp. *apii* susceptible celery or celeriac with deposit NCIMB 43699.

The present invention further relates to a methods for identifying a genomically encoded resistance against the plant pathogen *Fusarium oxysporum* f. sp. *apii* race 4 as found in *Apium graveolens* plant deposited under deposit number NCIMB 43699, the method comprises the step of detecting one genomic region, a combination of at least two genomic regions or a combination of at least three genomic regions, one genomic region is located on linkage group 4 between 28 and 33 cM; one genomic region is located on linkage group 5 between 56 and 60 cM; and one genomic region is located on linkage group 7 between 24 and 38 cM.

The present invention further also relates to seeds or plant parts of plants defined above or to seeds capable of providing the present plants and to molecular markers which markers co-segregate with a genomically-encoded resistance against the plant pathogen *Fusarium oxysporum* f. sp. *apii* as present in deposit NCIMB 43699.

The present invention furthermore relates to molecular markers which markers co-segregate with a genomically encoded resistance/susceptibility against the plant pathogen *Fusarium oxysporum* f. sp. *apii* as present in deposit NCIMB 43699, which molecular markers are selected from the group consisting of SEQ ID No. 1 until 10, SEQ ID No.'s linkage group 11 until 28 and SEQ ID No.'s 29 until 36.

EXAMPLES

Example 1. General Protocol for Assessing Resistance

The pathogen *Fusarium oxysporum* f. sp. *apii* race 4 (hereafter Foa4) is stored in glycerol at −80° C. Two weeks before the start of the disease trial, isolates are taken from the −80° C. and grown on potato dextrose agar (PDA) plates at 25° C. Five days before inoculation, the Foa4 isolates are transferred to liquid Czapek-Dox yeast (CDBY) broth and incubated at 25° C. One day before inoculation, the CDBY Foa4 spore suspension is centrifuged and resuspended in water. Spore concentration is adjusted to 106 spores/ml.

Per genotype, twenty 4-week-old seedlings are transplanted in 10×10 cm square pots containing soil. The plants are then grown at 20° C. with a 16 h/8 h light/dark period under greenhouse conditions. As a control, the Foa4-susceptible varieties Daybreak and Golden Spartan were used.

The celery seedlings are inoculated with the Foa4 spore suspension by injection. Six-week-old seedlings are injected with 5 ml spore suspension. Inoculation is repeated after one week. After the first inoculation, the temperature in the greenhouse is raised to 25° C., while maintaining a 16 h/8 h light/dark period.

Assessment of the plants occurs 7 weeks after the first inoculation. Plants are cut to determine the degree of internal browning. Plants are scored from 0 to 9. A score of '0' means the plant died and, therefore, is susceptible. A score of '9' means the plant does not have any internal browning and, therefore, is resistant.

Example 2. Results of Assessment for Resistance Against *Fusarium oxysporum* f Sp. *Apii* Race 4

| Cultivar | Score for Foa2 | Score for Foa4 |
|---|---|---|
| Golden Spartan | 0.7 | 0 |
| Daybreak | 0 | 0 |
| Merengo | 9 | 0.9 |
| NCIMB 43699 | 9 | 7 |

Example 3. Production of F1 Seed Applying CMS

One of the requisites for a modern hybrid variety is that inbreeding, resulting in off type plants, is minimized. In celery, a reliable system for hybrid production is available based on cytoplasmic male sterility. Applying this feature for seed production with male and female parent lines, hybrids essentially are resulting 100% from pure cross pollinations.

Example 4 Molecular Characterization of Genomically Encoded Resistance Against *Fusarium oxysporum* f. Sp. *Apii* Race 4 in *Apium graveolens*

An F1S1 population was made by crossing the source of resistance to a susceptible celery line, after which the resulting F1 plant was self-pollinated.

At least 2000 seeds were harvested from the F1S1 generation of a cross between the distinctive source of resistance and a susceptible celery line. To perform a QTL mapping, 900 plants of the cross were grown in the glasshouse and tested for Foa4 resistance. From each individual plant, leaf material was used for DNA isolation and successive marker analysis.

Using SNP markers covering the entire genome, QTLs were found on linkage group 4 (LG4), linkage group 5 (LG5), and linkage group 7 (LG7). These QTLs are defined by the SNP markers listed in the tables below.

| SNP | Internal Pat_ID | Linkage Group | Position on Linkage Group (cM) | Allele linked to resistance | Alternative allele |
|---|---|---|---|---|---|
| 1 | 5855 | 4 | 28.361 | G | A |
| 2 | 3253 | 4 | 30.397 | C | T |
| 3 | 0172 | 4 | 30.640 | C | G |
| 4 | 2779 | 4 | 31.691 | A | G |
| 5 | 6114 | 4 | 32.369 | G | A |
| 6 | 2283 | 5 | 56.793 | A | G |
| 7 | 1764 | 5 | 57.173 | T | C |
| 8 | 1049 | 5 | 57.670 | C | A |
| 9 | 4340 | 5 | 58.216 | C | T |
| 10 | 5397 | 5 | 58.292 | T | A |
| 11 | 5832 | 5 | 58.371 | C | T |
| 12 | 4999 | 5 | 58.530 | G | A |
| 13 | 2817 | 5 | 58.971 | C | T |
| 14 | 3869 | 5 | 59.024 | G | A |
| 15 | 0386 | 7 | 24.982 | C | T |
| 16 | 0654 | 7 | 25.330 | T | C |
| 17 | 4676 | 7 | 27.722 | G | A |
| 18 | 1133 | 7 | 37.668 | C | T |

| SEQ ID No. | LG* | Position on linkage group (cM) | Sequence -SNP nucleotide is highlighted bold and in brackets |
|---|---|---|---|
| SEQ ID No. 1 | 4 | 28.361 | GCTGTTGGGTGGGAGAGAGTATGGAAGAGTTTACAAAGGATGG GTTCAGG[**G**]GAAGACGTACACCCCGTCTAGGCACGATGTTGGAA CAACCATTGCAGTTA |
| SEQ ID No. 2 | 4 | 28.361 | GCTGTTGGGTGGGAGAGAGTATGGAAGAGTTTACAAAGGATGG GTTCAGG[**A**]GAAGACGTACACCCCGTCTAGGCACGATGTTGGAA CAACCATTGCAGTTA |

-continued

| SEQ ID No. | LG* | Position on linkage group (cM) | Sequence -SNP nucleotide is highlighted bold and in brackets |
|---|---|---|---|
| SEQ ID No. 3 | 4 | 30.397 | AACAGGAACCACACGTGGTTTCCCTTCATGAGAAACAGGACCATT<br>AGGTG[**C**]CTTCTGTTTATGACATGAAGCAGGAATATTAGTTGGCT<br>TAGGTTTCTTAG |
| SEQ ID No. 4 | 4 | 30.397 | AACAGGAACCACACGTGGTTTCCCTTCATGAGAAACAGGACCATT<br>AGGTG[**T**]CTTCTGTTTATGACATGAAGCAGGAATATTAGTTGGCT<br>TAGGTTTCTTAG |
| SEQ ID No. 5 | 4 | 30.640 | TGTTTAGAGGCAAGAAATCAAGAAAAGATGAAATCTTGGGGATT<br>TTTAGT[**C**]TGTGTTTGTSTGTGTGTGAATTGGGTTGGAGTGAATTC<br>TTGGTAAAAAGA |
| SEQ ID No. 6 | 4 | 30.640 | TGTTTAGAGGCAAGAAATCAAGAAAAGATGAAATCTTGGGGATT<br>TTTAGT[**G**]TGTGTTTGTSTGTGTGTGAATTGGGTTGGAGTGAATTC<br>TTGGTAAAAAGA |
| SEQ ID No. 7 | 4 | 31.691 | ACGACAAATTACTACAGTTTGCTTCAATCTTGCCAAATCGTGTGAA<br>GCTA[**A**]CACATGTTGAAATACCATGTCCTTTTCTATTTTTAAAGTTA<br>TCGTTTTAG |
| SEQ ID No. 8 | 4 | 31.691 | ACGACAAATTACTACAGTTTGCTTCAATCTTGCCAAATCGTGTGAA<br>GCTA[**G**]CACATGTTGAAATACCATGTCCTTTTCTATTTTTAAAGTT<br>ATCGTTTTAG |
| SEQ ID No. 9 | 4 | 32.369 | GTGTTAGAGTTAACAAAGTTGGCAGAAACCAAGTGCACTGATCCA<br>ACGTT[**G**]TGGGCTAYAGAAGTGTCAACTACTTTAAACTCAGCTGC<br>AGTGGACTTGCC |
| SEQ ID No. 10 | 4 | 32.369 | GTGTTAGAGTTAACAAAGTTGGCAGAAACCAAGTGCACTGATCCA<br>ACGTT[**A**]TGGGCTAYAGAAGTGTCAACTACTTTAAACTCAGCTGC<br>AGTGGACTTGCC |
| SEQ ID No. 11 | 5 | 56.793 | CACAAACCCCCCTTCATTTCATTTCTCATTTCTCATTTCTCATTTCTC<br>AC[**A**]ATTCACTCAACTCTCTCGTAATCTCCGATCCCAATTTCACCCC<br>CACAATG |
| SEQ ID No. 12 | 5 | 56.793 | CACAAACCCCCCTTCATTTCATTTCTCATTTCTCATTTCTCATTTCTC<br>AC[**G**]ATTCACTCAACTCTCTCGTAATCTCCGATCCCAATTTCACCCC<br>CACAATG |
| SEQ ID No. 13 | 5 | 57.173 | AAGTACCTGTTCTAGTGAGTTTATCTACCTCCTGTCAATCTTTTTCC<br>TTT[**T**]TTGTTTTCTGGTACTTGGACCAAAACCCCAAGTGTATAAAC<br>GTCAGGTCT |
| SEQ ID No. 14 | 5 | 57.173 | AAGTACCTGTTCTAGTGAGTTTATCTACCTCCTGTCAATCTTTTTCC<br>TTT[**C**]TTGTTTTCTGGTACTTGGACCAAAACCCCAAGTGTATAAAC<br>GTCAGGTCT |
| SEQ ID No. 15 | 5 | 57.670 | GGGACATAGCATTCAGGATTTATAAGAGTCTGGAAAGTGCTATTT<br>TCACC[**C**]CCCACAAGATCCTGAAGTGCAATCTCAATAATTCTTTCA<br>TTCTCCCTGCT |
| SEQ ID No. 16 | 5 | 57.670 | GGGACATAGCATTCAGGATTTATAAGAGTCTGGAAAGTGCTATTT<br>TCACC[**A**]CCCACAAGATCCTGAAGTGCAATCTCAATAATTCTTTCA<br>TTCTCCCTGCT |
| SEQ ID No. 17 | 5 | 58.216 | ATAGAGAAGGATATAACAAAATATTGGAAAATGCCAAGCCCCGA<br>AATGAT[**C**]CATATGGGAGGCATTTATCTGCCTTTACCTACCTCCGG<br>CTCAGCTCCTTG |
| SEQ ID No. 18 | 5 | 58.216 | ATAGAGAAGGATATAACAAAATATTGGAAAATGCCAAGCCCCGA<br>AATGAT[**T**]CATATGGGAGGCATTTATCTGCCTTTACCTACCTCCGG<br>CTCAGCTCCTTG |
| SEQ ID No. 19 | 5 | 58.292 | TACCATATGACTGTGCCGAGGGAGGAAATGCAAGCAGAAGTCCT<br>AGTTTT[**T**]AAATTCCAAGGTGTGGCAGTAGTCCCAGTGAGTGTCG<br>TATTGTAGATTTT |

-continued

| SEQ ID No. | LG* | Position on linkage group (cM) | Sequence -SNP nucleotide is highlighted bold and in brackets |
|---|---|---|---|
| SEQ ID No. 20 | 5 | 58.292 | TACCATATGACTGTGCCGAGGGAGGAAATGCAAGCAGAAGTCCT AGTTTT[**A**]AAATTCCAAGGTGTGGCAGTAGTCCCAGTGAGTGTCG TATTGTAGATTTT |
| SEQ ID No. 21 | 5 | 58.371 | ATCTCCAGAGTCGTTGCCACAGCTGGCAGAGATTGCTAGGAATCC TGCTG[**C**]TTTATCTGAACTTACTGTTGGGAAAGAGGATAACTTGA GACATTCTAGAG |
| SEQ ID No. 22 | 5 | 58.371 | ATCTCCAGAGTCGTTGCCACAGCTGGCAGAGATTGCTAGGAATCC TGCTG[**T**]TTTATCTGAACTTACTGTTGGGAAAGAGGATAACTTGA GACATTCTAGAG |
| SEQ ID No. 23 | 5 | 58.530 | CAGAAATATGATGCTTAGATATGGTCTTACTGTTACCATACTATTA ACCC[**G**]TTAAAAGCAAATATGTTAGGAGACCAATTACAACAAAAA GATCACCACCA |
| SEQ ID No. 24 | 5 | 58.530 | CAGAAATATGATGCTTAGATATGGTCTTACTGTTACCATACTATTA ACCC[**A**]TTAAAAGCAAATATGTTAGGAGACCAATTACAACAAAAA GATCACCACCA |
| SEQ ID No. 25 | 5 | 58.971 | TTAAAGCCTCTTATGCAACCAAGTAACAAAAATCAAAAGTGAGGA TTCGA[**C**]CTAATTGGATTTGAATTTGGGAGTTTTGAAATCTAAGGT TGAATTTGGGG |
| SEQ ID No. 26 | 5 | 58.971 | TTAAAGCCTCTTATGCAACCAAGTAACAAAAATCAAAAGTGAGGA TTCGA[**T**]CTAATTGGATTTGAATTTGGGAGTTTTGAAATCTAAGGT TGAATTTGGGG |
| SEQ ID No. 27 | 5 | 59.024 | ATATCCCCTTGGGTGGAGCTACTCTTAGTTGCGCAGCACTTATTTA GCTT[**G**]TTTTGGAAGGTGTCCAAAAACAAATTCATTAGGTCTGCTT AGCAAAGCCC |
| SEQ ID No. 28 | 5 | 59.024 | ATATCCCCTTGGGTGGAGCTACTCTTAGTTGCGCAGCACTTATTTA GCTT[**A**]TTTTGGAAGGTGTCCAAAAACAAATTCATTAGGTCTGCTT AGCAAAGCCC |
| SEQ ID No. 29 | 7 | 24.982 | TTTTGTGCGGATTGTAGTAAAAAACTTGGCTGTCAAGTATTCGAG TACTT[**C**]RAAAAATTCAGACACTTCATTTTACTGCAAGATGAAGAT CAAGAATCTCG |
| SEQ ID No. 30 | 7 | 24.982 | TTTTGTGCGGATTGTAGTAAAAAACTTGGCTGTCAAGTATTCGAG TACTT[**T**]RAAAAATTCAGACACTTCATTTTACTGCAAGATGAAGAT CAAGAATCTCG |
| SEQ ID No. 31 | 7 | 25.330 | TAATGAGCGTGAGGTGGAAGCAGCTGGGAATGGAAATTTAACCT CCAATG[**T**]AGAAAAGAGTTCTAATGGTCAATTAGAAACAAAAAA |
| SEQ ID No. 32 | 7 | 25.330 | TAATGAGCGTGAGGTGGAAGCAGCTGGGAATGGAAATTTAACCT CCAATG[**C**]AGAAAAGAGTTCTAATGGTCAATTAGAAACAAAAAA |
| SEQ ID No. 33 | 7 | 27.722 | GCAAAAGTAGGCTCCTGACATTGTACTTATATAAATTGCACTTTAC TGAA[**G**]GCGTAATTCTTCTACTACTAATCTGGAATCCAGTCTAAAG AGCCACTGTG |
| SEQ ID No. 34 | 7 | 27.722 | GCAAAAGTAGGCTCCTGACATTGTACTTATATAAATTGCACTTTAC TGAA[**A**]GCGTAATTCTTCTACTACTAATCTGGAATCCAGTCTAAAG AGCCACTGTG |
| SEQ ID No. 35 | 7 | 37.668 | AAGGAAGAAATCACCAGTGGCYTCAGCAAATGACTTTTTGGGAG GTGGGG[**C**]AGGAGAGAGATTTGGGGGAGGTGAAGATGAGGCTT TGATGAGGTGGAGGT |
| SEQ ID No. 36 | 7 | 37.668 | AAGGAAGAAATCACCAGTGGCYTCAGCAAATGACTTTTTGGGAG GTGGGG[**T**]AGGAGAGAGATTTGGGGGAGGTGAAGATGAGGCTT TGATGAGGTGGAGGT |

*LG-linkage group

Deposit Information

A sample of *A. graveolens* 1960176 with resistance to *Fusarium oxysporum* as described herein was deposited at the NCIMB (National Collections of Industrial, Food and Marine Bacteria (NCIMB), NCIMB Limited, Ferguson Building; Craibstone Estate, Bucksburn Aberdeen, Scotland, AB21 9YA United Kingdom) on Nov. 30, 2020 under number NCIMB 43699.

The invention claimed is:

1. A hybrid *Apium graveolens* plant, representative seed having been deposited under NCIMB 43699, wherein the plant is resistant to the plant pathogen *Fusarium oxysporum* f. sp. *Apii* race 4 and wherein the resistance is encoded by a combination of at least two genomic regions, a first genomic region, located on linkage group 4 between 28 and 33 cM; and a second genomic region, located on linkage group 5 between 56 and 60 cM, wherein said first genomic region, located on linkage group 4, is characterized by one or more sequences selected from the group consisting of SEQ ID Nos. 1, 3, 5, 7 and 9; and wherein said second genomic region, located on linkage group 5, is characterized by one or more sequences selected from the group consisting of SEQ ID Nos. 11, 13, 15, 17, 19, 21, 23, 25 and 27.

2. The *Apium graveolens* plant according to claim 1, wherein the resistance is encoded by a combination of at least three genomic regions, a third genomic region, located on linkage group 7 between 24 and 38 cM.

3. The *Apium graveolens* plant according to claim 2, wherein said third genomic region, located on linkage group 7, is characterized by one or more sequences selected from the group consisting of SEQ ID Nos. 29, 31, 33 and 35.

4. The *Apium graveolens* plant according to claim 2, wherein said combination of at least three genomic regions is characterized by SEQ ID Nos. 1, 3, 5, 7, 9, 11, 13, 15, 17, 19, 21, 23, 25, 27, 29, 31, 33 and 35.

5. The *Apium graveolens* plant according to claim 1, wherein the plant is selected from the group consisting of *Apium graveolens* var. *secalinum, Apium graveolens* var. *dulce*, and *Apium graveolens* var. *rapaceum.*

6. A hybrid celery or celeriac obtained by crossing a *Fusarium oxysporum* susceptible celery or celeriac with an *Apium graveolens* plant according to claim 1.

7. A method for identifying a genomically encoded resistance against the plant pathogen *Fusarium oxysporum* f. sp. *Apii* race 4 as found in *Apium graveolens* plant deposited under deposit number NCIMB 43699, comprising detecting a combination of at least two genomic regions, a first genomic region, located on linkage group 4 between 28 and 33 cM and a second genomic region, located on linkage group 5 between 56 and 60 cM, wherein said first genomic region, located on linkage group 4, is detected using one or more molecular markers selected from the group consisting of SEQ ID Nos. 1, 3, 5, 7 and 9, and said second genomic region, located on linkage group 5, is detected using one or more molecular markers selected from the group consisting of SEQ ID Nos. 11, 13, 15, 17, 19, 21, 23, 25 and 27.

8. The method according to claim 7, further comprising detecting a third genomic region, located on linkage group 7 between 24 and 38 CM, using one or more molecular markers selected from the group consisting of SEQ ID Nos. 29, 31, 33 and 35.

9. A seed or plant part of an *Apium graveolens* plant according to claim 1.

* * * * *